(12) United States Patent
Andrieux

(10) Patent No.: US 7,717,113 B2
(45) Date of Patent: May 18, 2010

(54) SYSTEM AND PROCESS FOR SUPPLYING RESPIRATORY GAS UNDER PRESSURE OR VOLUMETRICALLY

(75) Inventor: Claude Andrieux, Bordes (FR)

(73) Assignee: Nellcor Puritan Bennett LLC, Boulder, CO (US)

( * ) Notice: Subject to any disclaimer, the term of this patent is extended or adjusted under 35 U.S.C. 154(b) by 305 days.

(21) Appl. No.: 11/781,013

(22) Filed: Jul. 20, 2007

(65) Prior Publication Data

US 2008/0011300 A1 Jan. 17, 2008

Related U.S. Application Data

(63) Continuation of application No. 10/899,022, filed on Jul. 27, 2004, now abandoned.

(30) Foreign Application Priority Data

Jul. 29, 2003 (FR) .................................... 03 09347

(51) Int. Cl.
*A61M 15/00* (2006.01)
*A61M 16/00* (2006.01)
(52) U.S. Cl. ..................... 128/204.23; 128/200.24; 128/204.18; 128/204.21
(58) Field of Classification Search ............ 128/200.24, 128/204.18, 204.21, 204.23, 204.26
See application file for complete search history.

(56) References Cited

U.S. PATENT DOCUMENTS

| | | | | |
|---|---|---|---|---|
| 5,383,449 A * | 1/1995 | Forare et al. | ........... | 128/205.11 |
| 5,503,146 A | 4/1996 | Froehlich et al. | ....... | 128/204.23 |
| 5,535,738 A | 7/1996 | Estes et al. | ............. | 128/204.23 |
| 5,540,220 A * | 7/1996 | Gropper et al. | ........ | 128/204.23 |
| 5,546,933 A | 8/1996 | Rapoport et al. | ....... | 128/204.23 |
| 5,551,419 A * | 9/1996 | Froehlich et al. | ....... | 128/204.23 |
| 5,875,783 A | 3/1999 | Kullik | ................... | 128/204.18 |
| 6,095,139 A * | 8/2000 | Psaros | ................... | 128/204.22 |
| 6,131,571 A | 10/2000 | Lampotang et al. | .... | 128/204.21 |
| 6,152,132 A * | 11/2000 | Psaros | ................... | 128/204.25 |
| 6,543,449 B1 * | 4/2003 | Woodring et al. | ...... | 128/204.18 |
| 6,626,175 B2 * | 9/2003 | Jafari et al. | ............ | 128/204.21 |

(Continued)

FOREIGN PATENT DOCUMENTS

DE 197 14 644 A 10/1998

(Continued)

OTHER PUBLICATIONS

French Search Report, FR 0309347, 4 pages, Apr. 14, 2004.

*Primary Examiner*—Steven O Douglas
*Assistant Examiner*—Annette F Dixon

(57) ABSTRACT

The object of the invention is a device for supplying respiratory gas to a patient according to respiratory cycles, comprising a gaseous flow rate generator provided with a turbine with low inertia and high nominal speed, a first circuit called a supply circuit for the gaseous flow toward a respiratory mask or an intubation means of the patient, means for measuring pressure and/or measuring flow rate of the gaseous flow, computation means for parameters of pressure and/or flow rate, and means for controlling the speed of rotation of the generator, characterized in that the measuring means, the computation means and the speed control means coact automatically to control the speed of rotation of the turbine as a function of the inspiration and expiration phases and as a function of patient pressure signals and/or inspiration flow rate signals.

21 Claims, 1 Drawing Sheet

U.S. PATENT DOCUMENTS

| | | |
|---|---|---|
| 6,877,511 B2 * | 4/2005 | DeVries et al. ........ 128/204.26 |
| 2002/0005197 A1 | 1/2002 | DeVries et al. |
| 2002/0014239 A1 | 2/2002 | Chalvignac |
| 2002/0053345 A1 | 5/2002 | Jafari et al. |

FOREIGN PATENT DOCUMENTS

| | | |
|---|---|---|
| EP | 0 862 922 A | 9/1998 |
| EP | 1 243 282 A | 9/2002 |
| FR | 2 663 547 A1 | 12/1991 |
| FR | 2 822 384 A1 | 9/2002 |
| GB | 2 324 122 A | 10/1998 |
| WO | WO 00/24447 | 5/2000 |
| WO | WO 02/26305 A | 4/2002 |

* cited by examiner

SYSTEM AND PROCESS FOR SUPPLYING RESPIRATORY GAS UNDER PRESSURE OR VOLUMETRICALLY

RELATED APPLICATION

This application is a continuation of U.S. patent application Ser. No. 10/899,022, filed on Jul. 27, 2004, now abandoned which claims priority to French Application No. 03 09347 filed Jul. 29, 2003, the contents of which are hereby incorporated by reference in their entirety

TECHNICAL FIELD

The present invention relates to a device and process for supplying respiratory gas.

BACKGROUND

Devices for supplying respiratory gas are used particularly in the treatment of respiratory ailments of adult or infant patients.

Such devices are adapted to supply a quantity of air, if desired with added oxygen, either in the form of a quantified breathable volume, or in the form of a first predetermined pressure called inspiration pressure and a second predetermined pressure called expiration pressure.

WO 00/24447 relates to a device for supplying respiratory gas provided with a compressor delivering a flow of gas under pressure to a patient through a downstream accumulator/silencer and a flow rate regulating valve. According to this document, the surplus of unneeded gas is returned to an upstream filter/accumulator through a bypass valve so as to limit the loss of respiratory gas.

FR 2 663 547 A1 relates to apparatus for continuously providing an overpressure of respiratory gas; this apparatus using a high speed turbine supplying gas under constant predetermined pressure regulated by measuring the pressure at the respiratory mask of the patient. This apparatus is passive in that the pressure is maintained continuously, the expiration phases being possible thanks to a calibrated loss at the respiratory mask of the patient.

FR 2 822 384 AI in the name of the applicant relates to a mixed pulmonary ventilator provided with a flow generator, the circulation means permitting re-injecting the flow upstream of the generator during an expiration phase of the patient, the circulation means comprising particularly a regulating valve comprising two flaps actuated by the same actuator permitting several modes of regulation and an optimization of the flow as a function of the inspiration and expiration phases. According to this document, the speed of rotation of the generator is maintained constant, the pressure in the patient circuit being controlled by the two flaps which permit return of the gas to the generator particularly during the expiration phases.

SUMMARY

It remains that the circuits and systems necessary to provide and to regulate levels of pressure and/or volumetric quantities of respiratory gas are complicated and cumbersome with the control of the flaps and valves being sensitive.

The present invention seeks to provide an improved device for supplying respiratory gas which automatically controls the turbine for inspiration and expiration phases and does not use a return system for gas upstream of the turbine, thereby simplifying the system, whilst permitting operation with a sealed circuit at the respiratory mask or of the intubation device of the patient during inspiration phases and loss during expiration phases.

To this end, the present invention relates to a device for supplying respiratory gas to a patient according to respiratory cycles comprising a gas for a generator, a circuit for bringing the gaseous flow to a respiratory mask or intubation device of the patient, means for measuring the pressure and/or for measuring the gaseous flow rate, means for computing the parameters of pressure and/or flow rate, and control means of the speed of rotation of the generator, in which device the measuring means act on the speed control means through computer means to automatically control the speed of rotation of the turbine as a function of inspiration and expiration phases as a function of patient pressure signals and/or inspiration flow rate signals.

The pressure measuring means may, in particular, comprise a patient pressure sensor and/or an expiration valve pressure sensor.

The flow rate measuring means may, in particular, comprise an inspiration flow rate sensor disposed adjacent the outlet of the generator.

The flow rate measuring means may comprise an expiration flow rate sensor in a patient return circuit.

In a particular embodiment, the device may comprise a passive member for generating a pressure drop in the supply circuit. This passive member may, in particular, be a non-return flap, if desired associated with a passive flap for admission of external air downstream of the non-return flap in the supply circuit.

According to a particular embodiment of the invention, the device comprises an expiration circuit provided with an expiration valve and a proportional electro-valve for controlling said expiration valve by application of a counter-pressure.

The invention relates moreover to a process for providing a respiratory gas according to respiratory cycles, comprising inspiration and expiration phases, according to which said measurement means and said computing means act on said speed control means to automatically control the speed of rotation of the turbine as a function of the pressure and/or volume standards, of the detection of the inspiration and expiration phases, of patient pressure signals and/or inspiration flow rate signals, the supply of the respiratory gas taking place as to pressure or as to volume.

The process may preferably comprise phases of pressure increase with pressure increase slopes effected by acceleration of the turbine.

More particularly, the transition between an inspiration phase and an expiration phase can be effected by controlled deceleration of the turbine.

The process may comprise, during expiration phases, a control of an expiration valve with a pressure regulating member of the first circuit, via a proportional electro-valve which is part of a second circuit, the valve being a part of a third circuit connected to the mask or to the intubation device.

Preferably, the computing means and the control means of the speed of rotation of the generator may adapt the speed of the turbine as a function of an expiration pressure threshold beyond a regulated loss by the expiration valve so as to create a rinsing flow rate in the first circuit.

More particularly, during insufflation phases corresponding to the inspiration phases, an expiration valve, which is a part of a third circuit connected to the mask or to the intubation device, may be controlled for following the pressure through a proportional electro-valve and a second circuit.

In a particular embodiment, the process may comprise a measurement of expiration flow rate and a measurement of inspiration flow rate.

Other advantages and characteristics of the invention will become apparent from a reading of the description which follows and of a non-limiting example of the invention.

DETAILED DESCRIPTION

Figure 1:
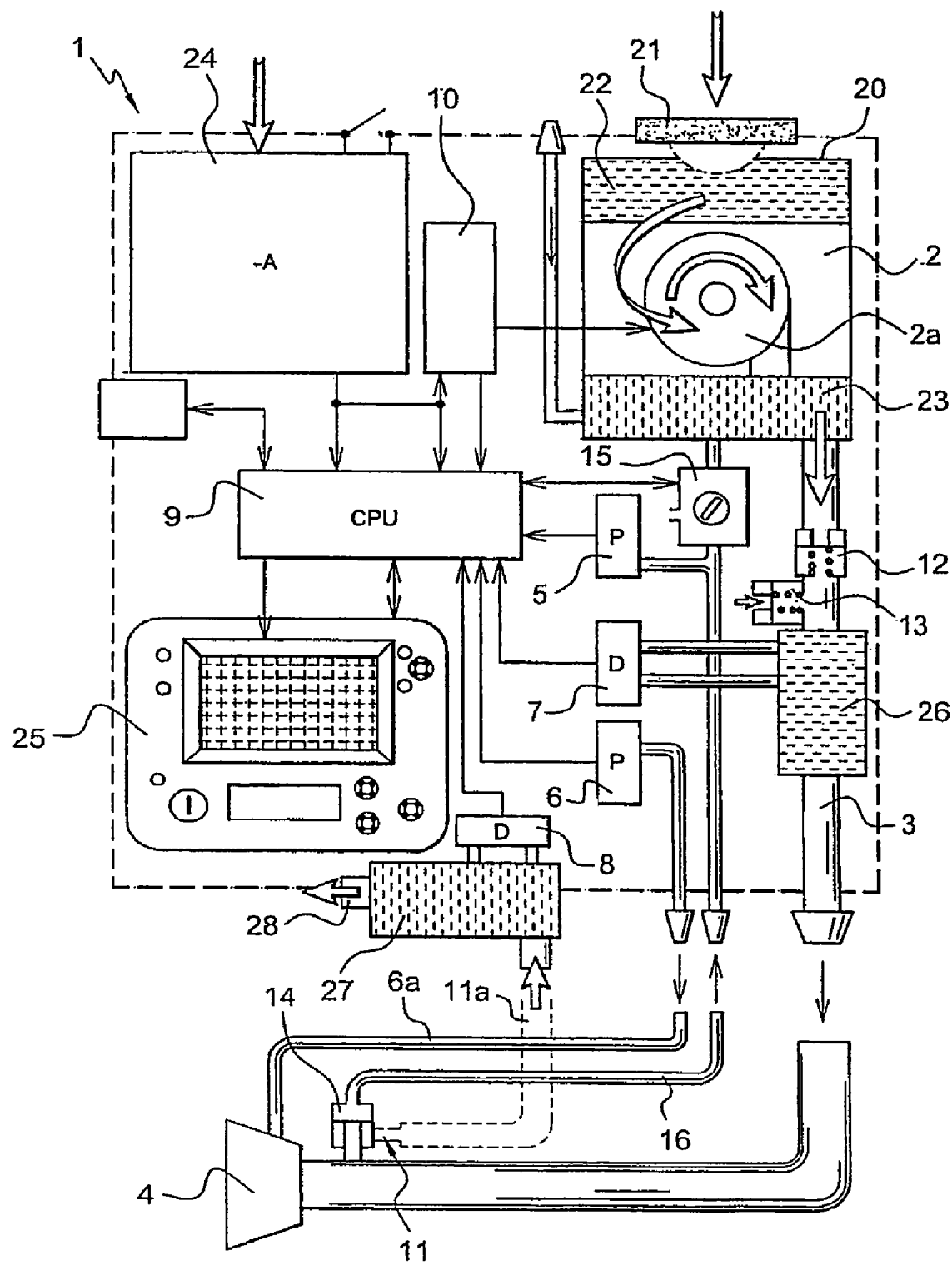
FIG. 1 is a schematic view of a device for supplying respiratory gas according to the invention.

The device 1 for supplying respiratory gas or ventilation device according to FIG. 1, comprises a generator 2 of gaseous flow provided with a turbine 2a of low inertia and high rate speed. This gaseous flow generator is disposed in a chamber 20, preceded by a filter 21 for ambient air inlet, by an upstream and downstream sound deadening means 22 and 23. The turbine 2a is for example a turbine with a maximum speed of rotation of the order of 50,000 rpm, adapted to supply a pressure of 70 millibar above ambient and a flow rate of the order of 200 l/min.

The air flow generator, thus comprises a micro-turbine with low inertia, driven by an electric motor, controlled by a computer or a computer means 9 so as to provide a wide range of flow rates and pressures.

At the outlet of the chamber 20, the generator is connected to a first circuit 3 called a circuit for supplying gaseous flow toward a respiratory mask 4 or a intubation device (not shown) of the patient.

The generator is controlled by control means 10 in the form of an electronic control card connected to a supply 24 and to computer means 9 in the form of an electronic card with a microprocessor provided with control software and connected to a control interface 25 with a screen and a keyboard.

So as to control the operation of the device and to cause it to operate, the computer means are connected to means 5, 6, 7, 8 for measuring the pressure and/or for measuring the flow rate of the gaseous flow in the form of sensors. The sensor 6 is a pressure sensor connected to a first circuit 3 which is a circuit for supplying gas to the mask 4 or intubation device of the patient.

According to the example, a sensor 6 is disposed in the apparatus 1 and connected to the mask 4 or to the intubation device via a tube 6a.

The sensor 5 is a pressure sensor connected to a second circuit 16 comprising a proportional electro-valve 15 whose operation will be described later.

The sensor 7 is an inspiration flow rate sensor disposed in the first circuit, in a laminator 26 controlling the flow of gas leaving the generator.

An expiration flow rate sensor 8, in the third circuit 11 called patient return circuit, completes the measurement means.

The computation means 9 controls the members such as the generator and the proportional electro-valve 15 as a function of standards entered into the interface 25 as a function of the ventilation programs and as a function of the pressure and/or flow rate parameters from the sensors.

According to the invention, the measuring means 5, 6, 7, 8, the computing means 9 and the speed control means 10 coact in the first instance automatically to control the speed of rotation of the turbine 2a as a function of the inspiration and expiration phases and as a function of the patient pressure signals and/or inspiration flow rate signals.

So as to regulate the output flow of the generator, the device according to FIG. 1 comprises a passive member 12 for generating a pressure drop in the supply circuit in the form of a non-return flap 12 mounted in the first circuit 3. Due to this member, the pressure on the generator side is always slightly greater than the pressure in the circuit 3 on the mask supply side or intubation device, which permits among other things a better regulation of the operation of the device.

Downstream of this non-return valve 12, the circuit 3 comprises a passive flap 13 for the admission of external air. This flap permits limiting the inspiration force of the patient by spontaneous respiration through the machine when the latter is not in operation.

On the mask side 4 of the intubation device after the circuit 3 for supplying gas, is located a third circuit 11 called an expiration circuit. This expiration circuit comprises an expiration valve 14 with a membrane permitting opening a passage either directly to the exterior or through tubing 11a toward a laminator 27 and an air outlet 28.

To the valve 14 is connected the second circuit 16 provided with proportional electro-valve 15 of the three-way type. This electro-valve 15 receives along a first path a pressure outlet of the generator, comprises a second path to vacuum and is connected by a third path to the valve 14.

The electro-valve permits controlling the valve 14 by applying a counter-pressure which closes the valve or limits its opening such that the expiration pressure will remain higher than the pressure of the second circuit 16. To release the valve 14, the electro-valve is controlled such that the pressure of the generator will be blocked, the second path of the free air being placed in communication with the third path.

Thus, a controlled expiration device is constructed about the expiration valve 14 controlled by the electro-valve 15 connected to the flow generator, this electro-valve 15 permitting sending a portion of the generated flow to the expiration valve so as to oppose its opening.

The proportional electro-valve 15 is controlled by control means coupled to the computation means 9 and, according to the example, disposed on the card receiving the computing means 9.

This device thus permits in operation, the control of the speed of the turbine 2a and the control of the expiration valve through the electro-valve to provide several modes of operation and particularly modes of volumetric operation. Thus, several modes of operation are sought and particularly modes of operation with inspiration and expiration pressure standards or modes for which a volume of air called a target volume is predetermined, or mixed modes.

The operation of the apparatus is based on a system of self-adaptive closed loop control of the speed of the flow generator. With this flow generator is associated a controlled expiration device, without a member for regulation of the supplemental principal flow.

In particular, the detection of an increasing slope of pressure can be translated by a level of acceleration of the turbine 2a and the detection of the transition between the inspiration phase and the expiration phase can be translated by a deceleration of the turbine 2a.

This control is effected by inspiration pressure or flow rate signals and according to control laws, based on proportional and integral coefficients, which differ according to the modes of ventilation, the adjustments of the pressure or flow rate and in particular the phases of the respiratory cycle.

The operation of the device and the associated ventilation process will be explained for example in the case of a mode in which an inspiration pressure Pi, an expiration pressure Pe, as well as a form of obtaining the inspiration pressure based on the time of pressure increase, are fixed. The time of insufflation is here dependent on a level of triggering the expiration adjusted on the basis of the measurement of a drop in flow rate measured in the inspiration detector 7, after obtaining a maximum insufflation flow rate available for the patient.

A limiting parameter for the time of insufflation is the minimum threshold corresponding to the slope of pressure measured; another parameter is a maximum threshold of safety for the insufflation time which corresponds to the last inspiration time carried out or at most to three seconds. Other safety parameters can be taken into account such as a safety frequency.

According to this embodiment, the objective of the insufflation phase is the establishment of a pressure level Pi with a variable time of increase and a holding time depending on the behavior of the associated flow rate.

The objective of the expiration phase is to maintain a pressure level Pe up to the beginning of the following inspiration phase, but also sufficiently to rinse the circuit so as to evacuate the residual expired gases.

To carry out inspiration cycles, the phases of pressure increase with increased slopes of pressure are carried out by an acceleration of the turbine 2a. The pressure is controlled in the inspiration pressure sensor 6.

During the insufflation phase corresponding to the inspiration phase, the computation means control the expiration valve 14, which is part of the third circuit 11 connected to the mask 4 or to the intubation device, via the proportional electro-valve 15 and the second circuit 16, according to pressure.

The transition between an inspiration phase and an expiration phase is effected by a controlled deceleration of the turbine 2a and the expiration valve 14, which is part of the third circuit 11 connected to the mask 4 or to the intubation device, is controlled, through the proportional electro-valve 15 and the second circuit 16, with a pressure regulation member of the first circuit 3.

During the expiration phase, the computation means and the means for controlling the speed of rotation of the generator adapt the speed of the turbine 2a as a function of an expiration pressure threshold beyond a loss regulated by the expiration valve 14 so as to create the rinsing flow rate of the first circuit. The non-return valve 12 and the spontaneous respiration valve 13 permit balancing the rinsing pressure which is maintained sufficiently low to limit the phenomenon of expiration braking without being canceled to avoid all heating of the turbine 2a.

In the case of ventilation for which a current volume as well as a frequency and a cycling ratio are fixed, the objective of the insufflation phase is the distribution of a current volume Vt with a suitable flow rate shape and during a time fixed by the frequency levels and the ratio of cycling regulated by the interface 25.

In this case, during insufflation, the patient current comprising the circuit 3, the mask 4 or intubation device is maintained sealed, against parasitic loss by the closing of the valve 14 controlled by the electro-valve 15. As a result, there is an increase in pressure of the circuit 3 and of the pulmonary system of the patient depending on the characteristics of the patient. In the case of exceeding the objective of maximum pressure measured with the pressure sensor 6, it is possible to cause the pressure in the control circuit 16 of the valve 14 by a command of the electro-valve 15 and to pass immediately into the expiration phase.

In the case of a target volume mode, the operator enters by the interface means a target volume standard into the computation means 9 which, as a function of this parameter and other parameters entered by the interface such as the frequency of minimum cycle and/or safety, cycling ratio, high pressure threshold, will permanently adjust the insufflation pressure between a low pressure threshold and a maximum pressure threshold so as to maintain the current volume inhaled by the patient as nearly as possible to a predefined target volume, namely for example between target volume Vt and target volume Vt+20%.

According to the target volume mode, it is particularly necessary to, at the same time, precisely adjust the pressure by pressure steps between the cycles. For example, for a pressure standard of the order of 20 millibars, the steps between cycles are defined between 0.5 millibar and 2 millibars so as to react immediately to the detection of an unbalance without having a strong reaction that would be uncomfortable to the patient.

This pressure adjustment is made according to the invention without a regulator device, such as the generator, but by controlling the speed of the turbine 2a of the generator 2 as a function of the pressure measurements of the sensor 6 of the pressure of the patient and by causing the operation of the expiration circuit comprising the expiration valve 14 following through the proportional electro-valve 15 in which, in this configuration, the flow generator is connected to the second circuit, the non-return flap 12 of the first circuit 3 permitting preserving a pressure slightly greater in the second circuit relative to the first circuit. Thus, the device permits providing a respiratory gas according to respiratory cycles comprising phases of inspiration and expiration, the measuring means 5, 6, 7, 8 and the computation means 9 acting on the speed control means 10 to automatically control the speed of rotation of the turbine 2a as a function of the pressure and/or volume standards, of the detection of inspiration and expiration phases, of patient pressure signals and/or inspiration flow rate signals.

With the device of the invention, the expiration valve 14 is controlled by the pressure during the inspiration phase and by a regulating member during the expiration phase.

The device according to the invention thus, permits ventilating a patient by pressure or volume with a patient circuit provided with an expiration device controlled by a simple control of the speed of the turbine.

I claim:

1. A system for supplying respiratory gas to a patient according to respiratory cycles, the system comprising:
   a housing,
   a turbine inside the housing,
   a patient inspiration flow outlet on the side of the housing and in flow communication with the turbine,
   an exhalation valve interface on the side housing,
   a proximal pressure interface on the side of the housing,
   an exhalation flow inlet on the side of the housing and defining a portion of an exhalation flow path,
   a first flow sensor inside the housing in flow communication with the patient inspiration flow outlet capable of generating a first flow signal,
   a first pressure sensor inside the housing in pressure communication with the proximal pressure interface capable of generating a first pressure signal,
   a second flow sensor inside the housing in flow communication with the exhalation flow inlet capable of generating a second flow signal indicating a flow rate through the exhalation flow path,
   a second pressure sensor inside the housing in pressure communication with the exhalation valve interface capable of generating a second pressure signal, wherein the exhalation valve interface and the second pressure sensor are located along an exhalation valve control path separate from the exhalation flow path, a central processing unit in electrical communication with the first and second pressure and flow sensors to receive pressure and flow signals therefrom, and a turbine speed controller board in electrical communication with the central processing unit and the turbine, wherein the central processing unit and the speed controller board coact to control the rotational speed of the turbine based on at least two pressure and/or a flow signals from the first and second pressure and flow sensors.

2. A system in accordance with claim 1, further comprising a valve inside the housing in pressure communication with the turbine, the exhalation valve interface, the second pressure sensor, and in electrical communication with the central processing unit.

3. A system in accordance with claim 1, further comprising at least one circuit connected to at least three of the patient inspiration flow outlet, the exhalation valve interface, the proximal pressure interface, and the exhalation flow inlet.

4. A system in accordance with claim 1, further comprising a non-return flap positioned between the turbine and the patient inspiration flow outlet to maintain a greater pressure on a turbine side of the flap than on an outlet side of the flap.

5. A system in accordance with claim 1, further comprising a passive flap positioned between the turbine and the patient inspiration flow outlet for the admission of external air.

6. A system in accordance with claim 1, further comprising an electro-valve located inside the housing in communication with the exhalation valve interface and in electrical communication with the central processing unit.

7. A system in accordance with claim 6, wherein the electro-valve is in direct fluid communication with the turbine.

8. A system in accordance with claim 1, further comprising a valve external to the housing in communication with the exhalation valve interface, the valve being controlled by gas pressure generated by the turbine.

9. A system in accordance with claim 1, further comprising a laminator positioned between the turbine and the patient inspiration flow outlet.

10. A system in accordance with claim 1, wherein the system does not include a return system for gas upstream of the turbine.

11. A system in accordance with claim 1, wherein the central processing unit is adapted to control the system for use with a sealed patient circuit.

12. A system in accordance with claim 1, wherein the central processing unit is adapted to control the system in accordance with multiple modes of ventilation.

13. A system in accordance with claim 1, wherein the central processing unit is adapted to control the system in accordance with a volume based mode of ventilation.

14. A system in accordance with claim 1, wherein the central processing unit is adapted to control the system in accordance with a pressure based mode of ventilation.

15. A system in accordance with claim 1, wherein the central processing unit and speed controller board are adapted to transition from an inhalation phase to an exhalation phase during ventilation by deceleration of the turbine.

16. A system in accordance with claim 1, wherein the central processing unit is adapted to compute an inspiration flow rate and an exhalation flow rate.

17. A system in accordance with claim 1, further comprising an inlet adapted for communication with a source external of the housing and the patient inspiration flow outlet.

18. A system in accordance with claim 1, further comprising sound deadening means positioned upstream and downstream of the turbine.

19. A system in accordance with claim 1, wherein the turbine comprises a micro-turbine adapted to provide a pressure of 70 millibar above ambient and a flow of the order of 200 liters/minute.

20. A method for supplying a respiratory gas to a patient, the method comprising:
    measuring a patient inspiration outlet flow along an inspiration flow path and providing a first flow signal;
    measuring a proximal interface pressure and providing a first pressure signal;
    measuring an exhalation inlet flow along an exhalation flow path and providing a second flow signal;
    measuring an exhalation pressure and providing a second pressure signal;
    controlling a flow generator based upon at least three of the first and second flow and pressure signals; and
    controlling an exhalation valve via an exhalation valve control path separate from the exhalation flow path, wherein the exhalation pressure is measured along the exhalation valve control path separate from the exhalation flow path.

21. A process in accordance with claim 20, further comprising controlling the flow generator based upon both the first and second flow signals and the first and second pressure signals.

* * * * *